(12) United States Patent
Bond

(10) Patent No.: US 6,736,637 B2
(45) Date of Patent: May 18, 2004

(54) PREMARKED ORTHODONTIC ARCH WIRE

(76) Inventor: James A. Bond, 2542 Damian Dr., Hatboro, PA (US) 19040

( * ) Notice: Subject to any disclaimer, the term of this patent is extended or adjusted under 35 U.S.C. 154(b) by 144 days.

(21) Appl. No.: 10/090,813

(22) Filed: Mar. 6, 2002

(65) Prior Publication Data

US 2002/0172910 A1 Nov. 21, 2002

Related U.S. Application Data

(60) Provisional application No. 60/291,321, filed on May 17, 2001.

(51) Int. Cl.$^7$ ................................................. A61C 3/00
(52) U.S. Cl. ............................................................ 433/20
(58) Field of Search ........................................ 433/20, 2

(56) References Cited

U.S. PATENT DOCUMENTS

| | | | | |
|---|---|---|---|---|
| 2,406,527 A | * | 8/1946 | Berke | 433/15 |
| 2,566,414 A | * | 9/1951 | Henry | 72/362 |
| 3,505,736 A | * | 4/1970 | Brader et al. | 433/20 |
| 3,667,129 A | * | 6/1972 | Aspel | 33/666 |
| 3,906,634 A | * | 9/1975 | Aspel | 433/24 |
| 3,916,526 A | * | 11/1975 | Schudy | 433/8 |
| 4,229,164 A | | 10/1980 | Robnett | 433/20 |
| 4,892,479 A | | 1/1990 | McKenna | 433/20 |
| 4,964,800 A | | 10/1990 | Good | 433/3 |
| 5,322,436 A | * | 6/1994 | Horng et al. | 433/23 |
| 5,722,827 A | | 3/1998 | Allesee | 433/20 |
| 5,910,008 A | | 6/1999 | Tran | 433/22 |

* cited by examiner

Primary Examiner—Ralph A. Lewis
(74) Attorney, Agent, or Firm—Gregory J. Gore

(57) ABSTRACT

An orthodontic arch wire composed of stainless steel or other bendable alloy formed into an arc is provided with lines permanently etched, or otherwise permanently marked, across its long dimension, and/or outward-facing surfaces at intervals approximating the midpoint at which adjacent teeth contact each other when normally aligned. When the arch wire is removed from the patient's mouth for periodic adjustments, the etch marks provide accurate, stable, and permanent landmarks for placement of adjustment bends for three-dimensional movements of individual teeth. In order to accommodate a range of tooth and dental arch sizes, the arch wires are of small, medium, and large sizes for both upper and lower arch forms with the markings proportioned for small, medium, and large tooth sizes.

5 Claims, 4 Drawing Sheets

PREMARKED ORTHODONTIC ARCH WIRE

The present application is related to provisional patent application serial No. 60/291,321 entitled "Premarked Orthodontic Archwire" filed on May 17, 2001, priority from which is hereby claimed.

FIELD OF THE INVENTION

The present invention relates to orthodontics and, in particular, intraoral arch wires employed as the force-transmitting member to move teeth.

BACKGROUND OF THE INVENTION

Modern orthodontic appliances consist of two main components: arch wires, which exert forces on the teeth, and attachments on the teeth called brackets or tubes. Arch wires are shaped by the manufacturer (preformed arch wires) or at chair-side by the orthodontist, into a curve resembling an ellipse or parabola which approximates the normal shape of the patient's dental arch. When an arch wire is secured in the slot of a bracket, or into a molar tube, it is elastically deformed. The force generated by the deformation is applied to the tooth, and is transmitted by the root of the tooth to the surrounding tissues. Bone remodeling occurs, allowing the tooth to move into better alignment with the other teeth. As alignment occurs, the arch wire becomes passive.

Before the introduction of preformed arch wires, the orthodontist fabricated the arch wire from a straight length of wire. In addition to placing the arch form in the wire, a number of other bends were necessary to accommodate the crown anatomy of the various teeth, since the machined brackets were all the same thickness from the tooth surface to the bracket slot. Prior to making the bends, marks were made while the arch wire was in the patient's mouth using an indelible pencil or wax china marker. The marks are used to located the bends.

The first preformed arch wires were introduced in the mid 1960s. Most were a basic U-shape, which saved the orthodontist time in forming a symmetrical arch wire from straight wire. In order to position the arch wire symmetrically in the mouth, a mid-line mark was necessary in the center of the arc. Soon arch wires were offered with midline marks painted on the wire or printed with FDA approved indelible ink. While these marks were helpful in the initial placement of the arch wires, they disappeared after the first visit. Fortunately, the routine arch wire bends acted as a guide to the correct positioning of the arch wire at future office visits. As technology advanced, some of the manufacturers permanently etched the midlines of their preformed arch wires. McKenna introduced a permanent midline mark bent into the arch wire in 1990 in the form of a U-shaped "dimple."

The introduction of the "straight-wire" appliance by Dr. Lawrence Andrews in 1972 made possible the reduction or elimination of many routine arch wire bends. His system included cast stainless steel brackets and tubes individualized for the different tooth anatomy. The goal was to produce ideal tooth alignment without routine anatomical or adjustment bends in the arch wire. Nevertheless, individual variations in tooth anatomy, imprecise placement of brackets on teeth, and other factors still made some adjustment bends necessary during treatment, especially during the finishing stages.

The use of the china marker or indelible pencil to mark arch wire bends was effective, but unhygienic. Neither instrument could be sterilized. Concern about the spread of HIV, hepatitis B, and other communicable diseases led to the introduction of the disposable arch wire marker. Like the china marker, it has a wax tip. However, the disposable marker resembles a thin wooden matchstick with its pointed end dipped in red wax. In order to adhere to the stick, maintain its shape, and make several marks on the arch wire, the composition of the wax material is different from that of the china marker, and it does not adhere as well to the arch wire in the mouth.

In practice, many of the marks shift, smear, or disappear during removal of the arch wire from the mouth. Others are rubbed off as bends are placed in the arch wire. A second or third visit to the mouth is usually necessary to mark all adjustment bends. Since adjustment bends are often very small, it is difficult to use them to orient the arch wire for subsequent marks or for arch wire placement in the mouth. Errors can result in which previous bends interfere with seating of the arch wire in the brackets. Occasionally an arch wire may be turned wrong side up when removed from the mouth, leading to adjustment errors and incorrect re-insertion into the mouth. These errors extend chair time with the patient and overall treatment time, as well as increasing patient discomfort and trauma to the teeth.

Current high quality preformed ideal arch wires are shaped into an arc with proportions similar to the anatomic shape of the dental arch. Most are provided with a midline mark that is either etched or painted. The etched marks are permanent but the painted midline marks soon disappear. Except for space closing arch wires that incorporate loops, or have hooks or tubes attached, preformed arch wires have no other markings to indicate where adjustment bends should be made.

SUMMARY OF THE INVENTION

In order to solve the problems in the dental arts described above, the present arch wire has been devised. Specifically, the arch wire comprises a preformed and premarked wire having a plurality of markings along a surface thereof. The marks may be applied to the arch wire by various permanent marking processes such as chemical etching, laser etching, or laser engraving. Preferably the markings are along a top surface of the arch wire or along the labial/buccal surface. In use, a premarked arch wire is selected from a group of arch wires of different sizes to match the size of the patient's dental arch. This conveniently places the permanent markings on the arch wire between the patient's teeth where adjustment bends need to be made.

A preformed arch wire with adjustment marks etched or otherwise permanently marked on the surface eliminates the above-described problems and the problem of cross-contamination, as well as greatly increasing efficiency. It is therefore an object of the present invention to provide an arch wire system to eliminate repeated arch wire insertions to replace lost, smeared, or drifted marks. It is a further object of the invention to permit arch wire adjustment bends to be made accurately and quickly with reduction in discomfort to the patient. Other objects and advantages of the invention will become apparent to those of skill in the art from the following drawings and description of the preferred embodiment.

DESCRIPTION OF THE PREFERRED EMBODIMENT

The following description refers primarily to an arch wire used for the later stages of orthodontic treatment. However, the preferred embodiment could be incorporated into other arch wire types made of a bendable alloy. For the sake of simplicity, an ideal "finishing" arch wire is illustrated.

Figure 1:
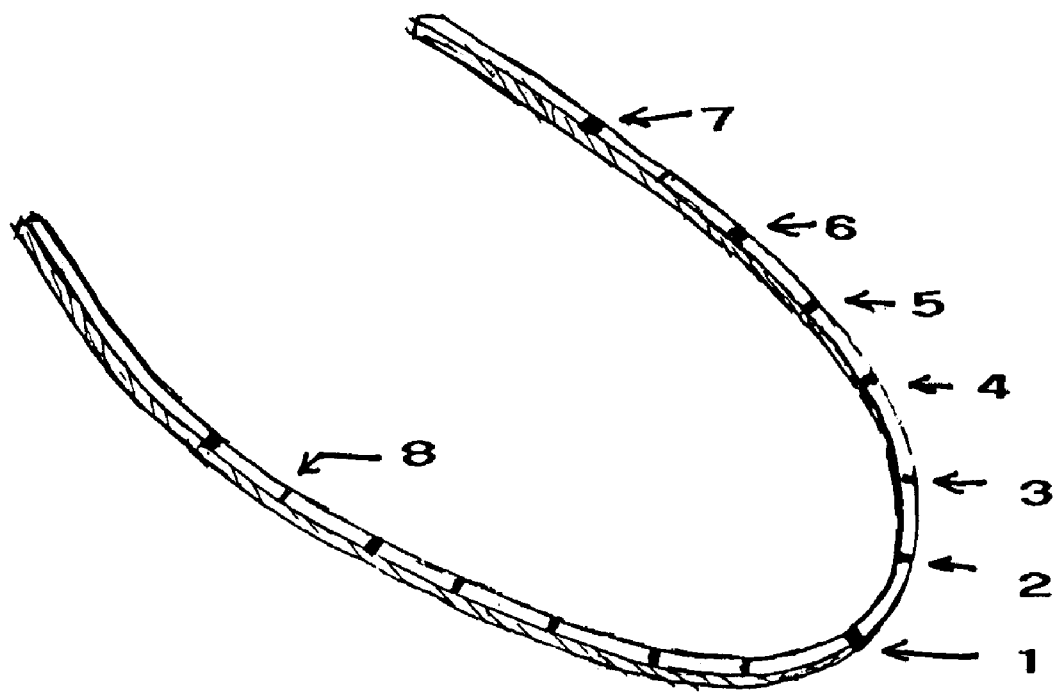
FIG. 1 is a perspective view of a maxillary arch wire of the present invention.

The illustration of the invention in FIG. 1 shows an upper arch wire with a conventional etched midline mark 1. Additional marks are permanently etched at locations 2, 3, 4, 5, 6, and 7 between the teeth where adjustment bends are usually made in the arch wire. For convenience, a double mark is placed between the second bicuspid and first molar at location 6, and a heavy single mark is placed between the first and second molars at location 7. If only the first molars are banded, the wire may be cut to length at location 7. A single mark is placed at location 8, one bicuspid width mesial to the mark between the molars. During closure of extraction spaces, the arch wire would slide distally, moving the mark at location 8 into position to replace the mark at 7 as the latter disappears into the second molar tube. The exact spacing of the marks are calculated so that they are aligned with the contact points of normally aligned adjacent teeth. The crown widths of the teeth would determine the measurements.

Figure 2:
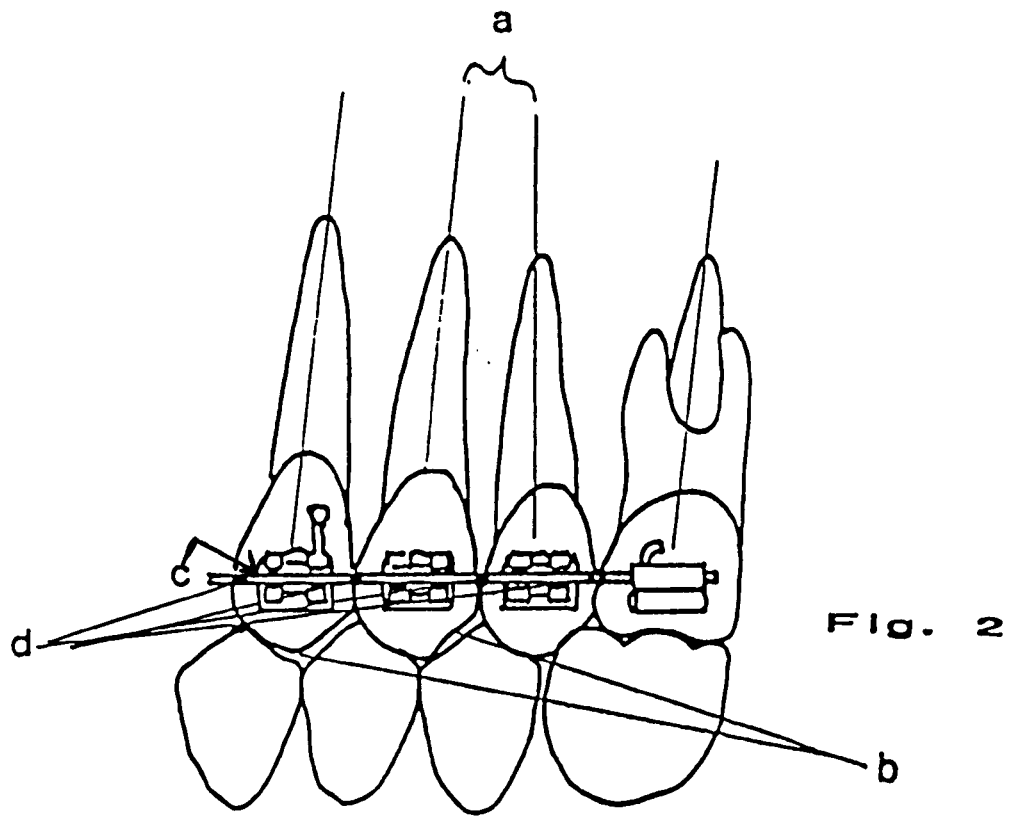
FIG. 2 is a side view of a patient's unsettled occlusion before placement of adjustment bends in the arch wire.
Figure 3:
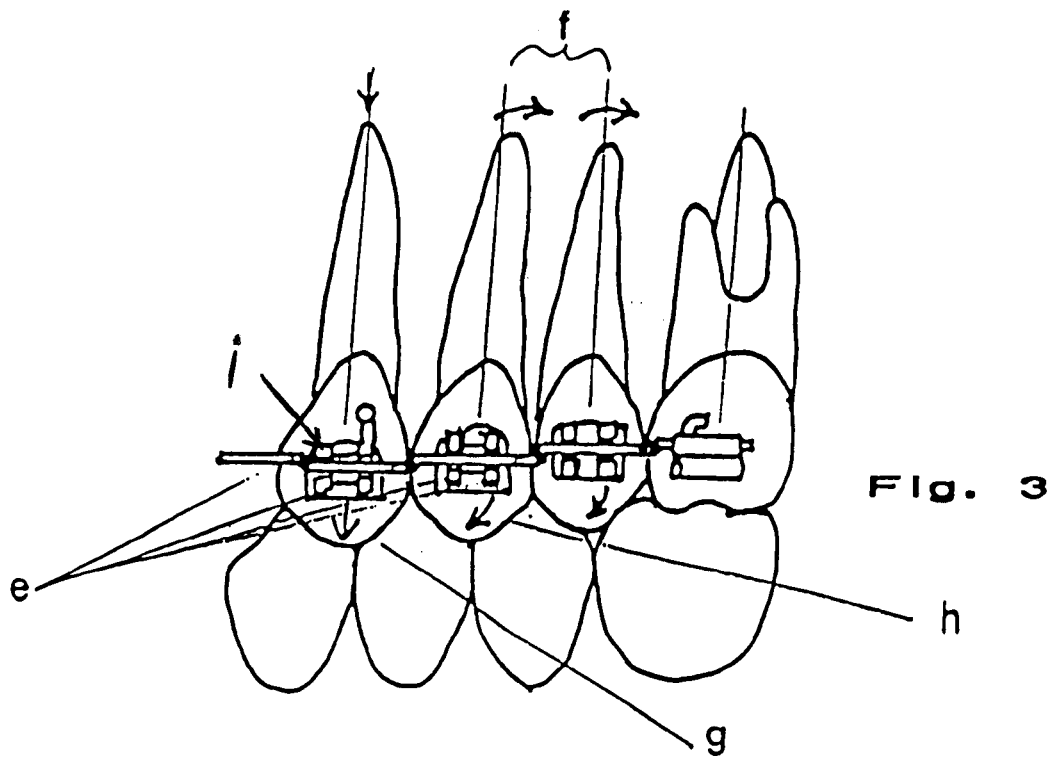
FIG. 3 is the same side view of FIG. 2 but with the patient's teeth seated into better occlusion after adjustment bends have been made in the arch wire.

FIG. 2 illustrates an unsettled posterior occlusion with an unadjusted ideal arch wire in place. The roots of the bicuspids "a" are too upright and bracket placement error at "c" has lifted the cuspid out of contact with the lower teeth. The result is an unsettled occlusion "b". Permanent arch wire marks "d" are extended to the buccal to indicate the location of adjustment bends. FIG. 3 illustrates a well-seated occlusion after adjustment bends "e" have been made in the arch wire at the permanent marks. The bucuspid root apices "f" have moved distally as indicated by the arrows, while the crowns "h" have rotated mesially and occlusally into better contact with the lower teeth. Step-down bends mesial and distal to the cuspid bracket "i" have moved the crown "g" into improved contact with the lower teeth.

Figure 4:
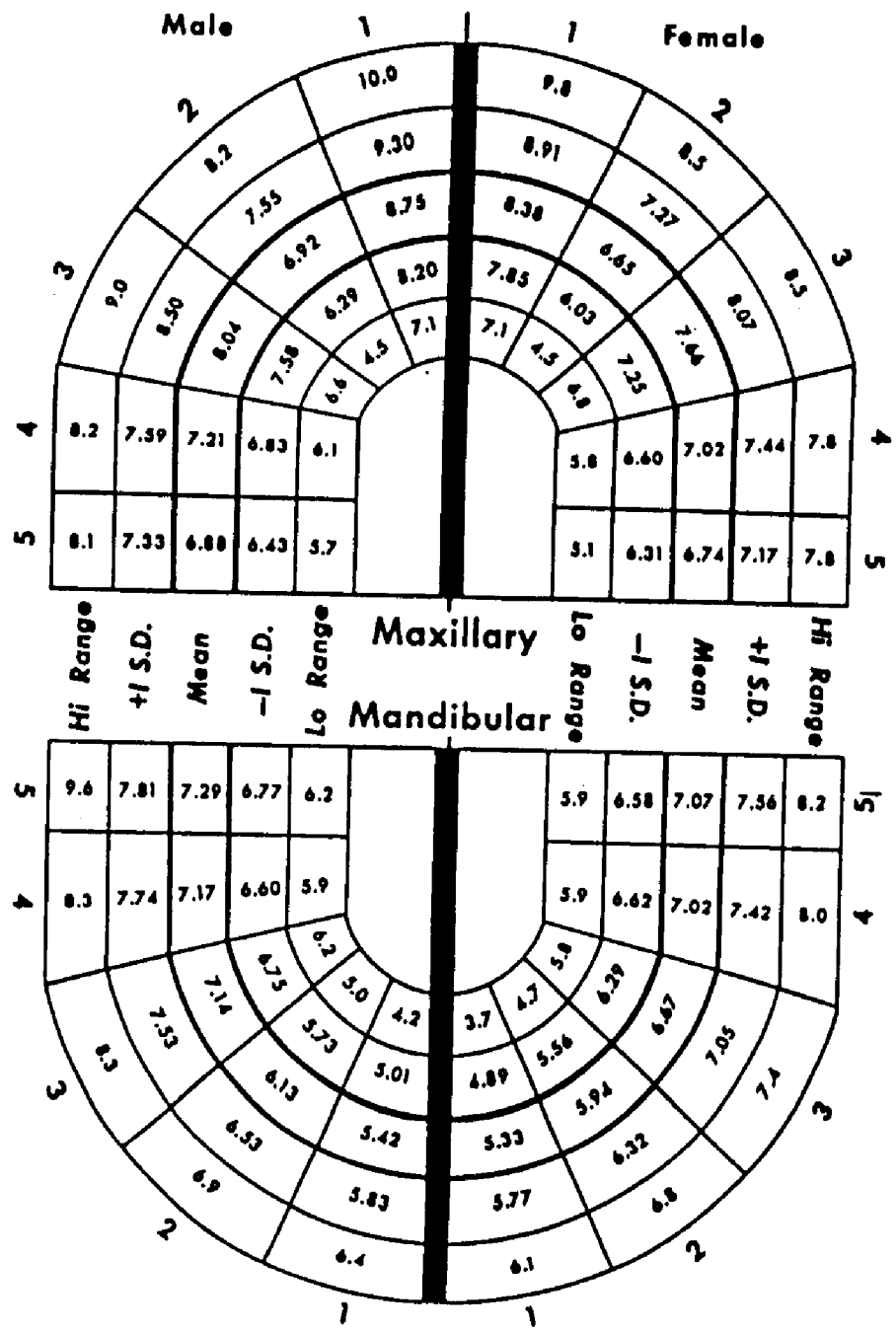
FIG. 4 is a table of tooth sizes.

In order to be sure that markings for adjustments toward the back of the mouth are not shifted forward for a patient with large teeth, or backward for a patient with small teeth, arch wires must be available with markings spaced to accommodate dental arches with small, medium, or large teeth. FIG. 4 shows that the difference between the widths of the largest and smallest maxillary (upper) central incisors in a study by Moorrees (1959) was 2.9 mm. The size range from the middle 68% (plus or minus one standard deviation) of the sample was only 1.1 mm. Two or three sets of proportionately marked arch wires should be sufficient to cover the range of tooth sizes from small to large. The Orthos system of computer engineered brackets and arch wires (Andrieiko, et al, 1995) currently offers upper and lower large and small arch wire forms to accommodate similar dental arch dimensions. The addition of permanent adjustment marks proportionate to this type of pre-sized arch wire is an example of the application of the preferred embodiment. Alternatively, a single size arch form can be used with marks in three different widths. The dentist can then adjust this arch form to fit the patient.

Preformed arch wires are usually formed from wire of rectangular, square, or round cross-sectional shape taken from a large spool and contoured into the desired arch form by a series of rollers, then cut to length. The permanent markings would be most efficiently placed on the arch wire before it is contoured. However, they may also be placed after the arch form has been placed.

Figure 5:
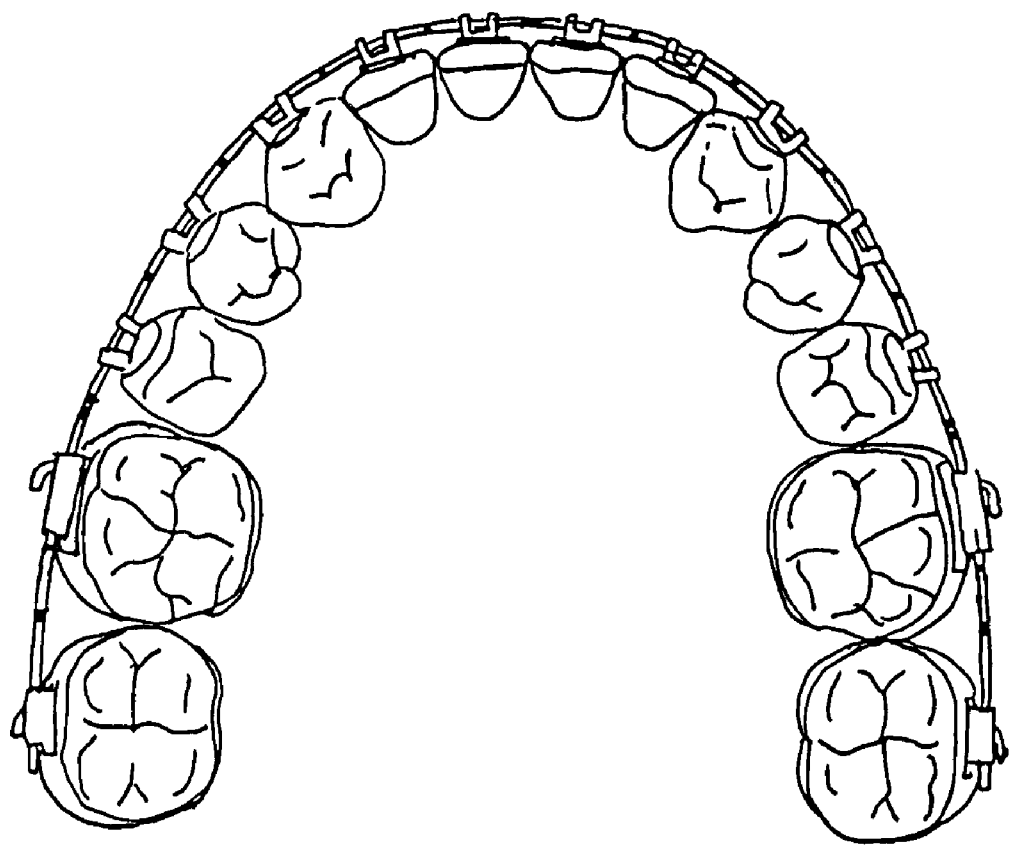
FIG. 5 is a top view of the mandibular version of the present invention engaged in the orthodontic brackets and molar tubes.

With reduction or elimination of routine arch wire bends and the use of bracket placement gauges to improve the accuracy of bracket placement, most adjustable bends can be subtle and should not take up excessive arch wire length. As a result, the marks should stay between the brackets of adjacent teeth and not interfere with arch wire insertion into the bracket slot. In FIG. 5 the lower arch wire with permanent adjustment marks is shown engaged in the brackets and tubes of a patient's mandibular arch.

The permanent adjustment marks are etched on the upward facing surfaces of the arch wires so that they can be seen as the arch wire is positioned in the mouth, and to eliminate confusion over which side of the arch wire is facing up during adjustment and insertion in the mouth. The marks may also be extended to the labial/buccal surface for increased visibility while bends are being placed. Since the distances between the marks on the upper arch will be wider than the distances in the lower arch, the upper and lower arch wires can be easily identified.

In certain cases of dental crowding, a bicuspid tooth is removed on each side of the dental arch to provide space for alignment of the other teeth. As the extraction space is closed, the premarked arch wire will shift distally on both sides of the mouth. The double mark between the second bicuspid and molar disappears into the first molar tube. It will be replaced by the mark originally between the bicuspids which has moved backward with space closure. When second molars have orthodontic tubes attached, the adjustment mark between the first and second molar will also be hidden inside the second molar tube during extraction space closure. Therefore, an additional mark (FIG. 1, location 8) is placed a bicuspid width forward of the first/second molar mark for use in this situation. This mark would usually be hidden by the first molar tube in non-extraction cases and only visible after space closure, thus eliminating confusion.

Occasionally, a patient will complain of the end of the arch wire being "long" and poking the cheek after the arch wire has been in place for several weeks. After the long end has been clipped, the arch wire is removed for adjustment and is found to be short on one side. The reason is that the wire had shifted to one side of the mouth, causing the projecting end to appear "long" when it wasn't. In the absence of bends in the wire, it was impossible to determine the cause of the problem without untying the arch wire. Examination of a premarked arch wire would reveal the cause of the problem and avoid untying or replacing the arch wire.

The single greatest advantage of the premarked arch wire is the decrease in patient chair time made possible by eliminating repeated arch wire insertions to replace lost, smeared, or drifted wax marks. Adjustment bends can be made accurately and quickly with a reduction in discomfort to the patient.

From the foregoing description of the invention it will be apparent that the objects of the invention have been achieved. Other modifications may be made which will be obvious to one of skill in the art from the description of the preferred embodiment, however the scope of the applicant's invention should be limited only by the following claims and legal equivalents.

What is claimed is:

1. An orthodontic arch wire, comprising:
   a preformed and premarked orthodontic arch wire having a plurality of markings along a surface thereof, each of said markings being permanent guide marks located in alignment with all of the contact points of normally aligned adjacent teeth, and being between the teeth where adjustment bends are made in the arch wire to forceably move teeth.

2. The arch wire of claim 1 wherein said marks are applied to said arch wire by a process from the group consisting of chemical etching, laser etching, or laser engraving.

3. The arch wire of claim 1 wherein said plurality of markings are along a top surface of said arch wire.

4. The arch wire of claim 1 wherein said plurality of markings is along a labial/buccal surface thereof.

5. The method of selecting an orthodontic arch wire for a dental patient, comprising:
   providing a plurality of arch wires of different sizes, each arch wire having a plurality of markings along a surface thereof, each of said markings being permanent guide marks located in alignment with all of the contact points of normally aligned adjacent teeth;
   sizing a patient's teeth; and
   selecting from among said plurality of arch wires, one arch wire best sized to the patient's tooth size such that when applied to said patient's teeth said guide marks are located between the patient's teeth where adjustment bends are to be made to forceably move teeth.

* * * * *